US009310315B2

(12) United States Patent
Zhang

(10) Patent No.: US 9,310,315 B2
(45) Date of Patent: *Apr. 12, 2016

(54) METHODS FOR DETECTING DEFECTS IN INORGANIC-COATED POLYMER SURFACES

(71) Applicant: LIFE TECHNOLOGIES CORPORATION, Carlsbad, CA (US)

(72) Inventor: Yu-Zhong Zhang, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 156 days.

This patent is subject to a terminal disclaimer.

(21) Appl. No.: 14/192,711

(22) Filed: Feb. 27, 2014

(65) Prior Publication Data
US 2014/0175305 A1 Jun. 26, 2014

Related U.S. Application Data

(60) Division of application No. 13/633,713, filed on Oct. 2, 2012, now abandoned, which is a continuation of application No. 12/808,325, filed as application No. PCT/US2008/087207 on Dec. 17, 2008, now Pat. No. 8,304,242.

(60) Provisional application No. 61/014,396, filed on Dec. 17, 2007.

(51) Int. Cl.
*G01N 31/22* (2006.01)
*G01N 21/91* (2006.01)
*C07F 5/02* (2006.01)

(52) U.S. Cl.
CPC .............. *G01N 21/91* (2013.01); *C07F 5/022* (2013.01); *Y10T 428/24355* (2015.01)

(58) Field of Classification Search
CPC . G01N 21/643; G01N 21/6489; G01N 21/91; G01N 21/94
USPC ...................................................... 436/1, 3, 5
See application file for complete search history.

(56) References Cited

U.S. PATENT DOCUMENTS

| 1,753,301 | A | 4/1930 | Pitschner |
| 2,079,925 | A | 5/1937 | Reichert |

(Continued)

FOREIGN PATENT DOCUMENTS

| EP | 1439384 | 7/2004 |
| GB | 795456 | 5/1958 |

(Continued)

OTHER PUBLICATIONS

Bryant, D. E. et al., "The Use of Fluorescent Probes for the Detection of Under-Film Corrosion", *Progress in Organic Coatings*, vol. 57(4), 2006, 416-420.

(Continued)

*Primary Examiner* — Arlen Soderquist
(74) *Attorney, Agent, or Firm* — Life Technologies Corporation

(57) ABSTRACT

Lipophilic fluorescent substances can be used to detect surface defects in materials having hydrophilic (e.g., inorganic) coatings. Use of the described methods makes surface defects appear fluorescent, while the remaining surfaces are not labeled. The disclosed methods are inexpensive, rapid, and easy alternatives to existing approaches.

14 Claims, 3 Drawing Sheets

(56) References Cited

U.S. PATENT DOCUMENTS

| | | | |
|---|---|---|---|
| 2,259,400 A | 10/1941 | Switzer | |
| 2,340,940 A | 2/1944 | De Forest | |
| 2,405,078 A | 7/1946 | Ward | |
| 2,635,329 A | 4/1953 | De Forest et al. | |
| 2,774,886 A | 12/1956 | De Forest et al. | |
| 2,920,203 A | 1/1960 | Switzer et al. | |
| 2,953,530 A | 9/1960 | Switzer et al. | |
| 3,164,006 A | 1/1965 | Alburger | |
| 3,490,873 A | 1/1970 | Corl | |
| 3,636,759 A | 1/1972 | Alburger | |
| 3,708,665 A | 1/1973 | Prine | |
| 3,735,131 A | 5/1973 | Sherwin | |
| 3,830,094 A | 8/1974 | Leger | |
| 3,892,690 A | 7/1975 | Setterstrom | |
| 3,958,119 A | 5/1976 | Shigekawa | |
| 4,002,905 A | 1/1977 | Molina | |
| 4,044,253 A | 8/1977 | Crane | |
| 4,054,535 A | 10/1977 | Molina | |
| 4,331,027 A | 5/1982 | Fijalkowski | |
| 4,400,618 A | 8/1983 | Bupp et al. | |
| 4,552,847 A | 11/1985 | Bauman | |
| 4,621,193 A | 11/1986 | Van Hoye | |
| 4,659,674 A | 4/1987 | Bauman et al. | |
| 4,692,347 A | 9/1987 | Yasuda | |
| 4,774,188 A | 9/1988 | Chandross | |
| 4,816,686 A * | 3/1989 | Hara | G01N 21/95684 250/458.1 |
| 4,916,711 A | 4/1990 | Boyer et al. | |
| 4,929,837 A * | 5/1990 | DiVita | G01N 21/952 250/302 |
| 4,968,892 A | 11/1990 | Mc Atee | |
| 4,976,826 A | 12/1990 | Tani | |
| 5,187,288 A | 2/1993 | Kang et al. | |
| 5,326,692 A | 7/1994 | Brinkley | |
| 5,667,840 A * | 9/1997 | Tingey | G01N 21/643 427/157 |
| 5,723,218 A | 3/1998 | Haugland et al. | |
| 5,723,976 A | 3/1998 | Yoshida et al. | |
| 5,786,219 A | 7/1998 | Zhang et al. | |
| 5,965,446 A | 10/1999 | Ishikawa | |
| 6,005,113 A | 12/1999 | Wu et al. | |
| 6,005,668 A | 12/1999 | Held et al. | |
| 6,014,209 A * | 1/2000 | Bishop | G01N 21/9501 356/237.5 |
| 6,097,484 A | 8/2000 | McIntosh et al. | |
| 6,097,784 A | 8/2000 | Tuy | |
| 6,190,759 B1 * | 2/2001 | Johansson | H05K 1/0269 174/258 |
| 6,270,572 B1 | 8/2001 | Kim et al. | |
| 6,327,410 B1 | 12/2001 | Walt et al. | |
| 6,342,400 B1 | 1/2002 | DePetrillo | |
| 6,427,544 B1 | 8/2002 | Sanders | |
| 6,616,712 B1 | 9/2003 | Beck et al. | |
| 6,620,670 B2 | 9/2003 | Song et al. | |
| 6,638,859 B2 | 10/2003 | Sneh et al. | |
| 6,677,584 B2 | 1/2004 | Yonushonis | |
| 6,916,221 B2 | 7/2005 | Kaltenbach et al. | |
| 6,943,902 B2 | 9/2005 | Borchardt et al. | |
| 7,059,665 B2 | 6/2006 | Murai et al. | |
| 7,449,336 B2 | 11/2008 | Tomt et al. | |
| 8,048,377 B1 | 11/2011 | Zhou et al. | |
| 8,304,242 B2 | 11/2012 | Zhang | |
| 2001/0028454 A1 * | 10/2001 | Savareigo | G01N 21/95692 356/237.5 |
| 2002/0135758 A1 * | 9/2002 | Potyrailo | C09K 11/06 356/237.2 |
| 2002/0162966 A1 | 11/2002 | Yoder | |
| 2004/0157333 A1 | 8/2004 | McAmish et al. | |
| 2004/0194691 A1 | 10/2004 | George et al. | |
| 2004/0203159 A1 | 10/2004 | Zander et al. | |
| 2004/0258927 A1 | 12/2004 | Conzone et al. | |
| 2005/0008944 A1 * | 1/2005 | Cerrina | B82Y 10/00 430/5 |
| 2005/0064209 A1 | 3/2005 | Haines | |
| 2005/0158862 A1 | 7/2005 | Tomt et al. | |
| 2005/0195389 A1 * | 9/2005 | Noy | G01N 21/956 356/237.2 |
| 2005/0202660 A1 | 9/2005 | Cohen | |
| 2007/0134420 A1 | 6/2007 | Koberstein et al. | |
| 2008/0144921 A1 * | 6/2008 | Lizotte | G01N 21/6456 382/145 |
| 2008/0145727 A1 | 6/2008 | Faidi et al. | |
| 2009/0084510 A1 | 4/2009 | Perry | |

FOREIGN PATENT DOCUMENTS

| | | |
|---|---|---|
| GB | 795779 | 5/1958 |
| GB | 844540 | 8/1960 |
| GB | 1178049 | 1/1970 |
| JP | 03-199938 | 8/1991 |
| JP | 03199938 | 8/1991 |
| JP | 04-140651 | 5/1992 |
| JP | 07-155567 | 6/1995 |
| JP | 07-270341 | 10/1995 |
| JP | 09-127105 | 5/1997 |
| JP | 2005-137227 | 6/2005 |
| JP | 2005-257684 | 9/2005 |
| JP | 2008-536264 | 9/2008 |
| WO | WO-2004/033397 | 4/2004 |
| WO | WO-2007/082376 | 7/2007 |
| WO | WO-2007/137292 | 11/2007 |

OTHER PUBLICATIONS

Carcia, P. F. et al., "Ca test of Al2O3 gas diffusion barriers grown by atomic layer deposition on polymers", *Applied Physics Letters*, vol. 89, 2006, 1-3.

Dunkel, Ralf, "Method of measuring ultra-low water vapor permeation for OLED displays", *General Atomics and Affiliated Companies*, Powerpoint presentation, 1-15.

Gai, H et al., *8th International Conference on Electronic Packaging Technology (ICEPT)*, 2007, 1-3.

Groner, M D. et al., "Low-Temperature Al2O3 Atomic Layer Deposition", *Chem Mater*, vol. 16, No. 4, 2004, 639-645.

Groner, M. D. et al., "Gas diffusion barriers on polymers using Al2O3 atomic layer deposition", *Applied Physics Letters*, vol. 88, 2006, 1-3.

Ke, L. et al., "Degradation Study in Flexible Substrate Organic Light-Emitting Diodes", *Applied Physics A: Materials Science & Processing*, vol. 81(5), 2005, 969-974.

Li, S. et al., "Mixed-mode cohesive-zone models for fracture of an adhesively-bonded polymer-matrix composite", *Engineering Fracture Mechanics*, vol. 73, No. 1, 2006, 64-78 (plus 14 figures).

Nisato, G. et al., "Evaluating High Performance Diffusion Barriers: the Calcium Test", *21st Annual Asia Display*, 8th International Display Workshop, Nagoya, Japan, 2001, 1-4.

Okamoto, K. et al., *Nano Letters*, vol. 4, 2004, 233-239.

Perng, D. B. , "A Novel AOI System for OLED Panel Inspection", *Journal of Physics: Conference Series*, vol. 13, 2005, 353-356.

Zhang, Yadong et al., "Fluorescence tag-based inspection of barrier coatings for organic light emitting diodes and polymer packages", *Nanotech 2008 Conference Program Abstract*, NSTI Nanotech: The Nanotechnology Conference and Trade Show, Boston, Jun. 1-5, 2008, 1-4.

\* cited by examiner

METHODS FOR DETECTING DEFECTS IN INORGANIC-COATED POLYMER SURFACES

CROSS REFERENCE TO RELATED APPLICATIONS

This application is a Division of U.S. application Ser. No. 13/633,713, filed Oct. 2, 2012, which is a Continuation of U.S. application Ser. No. 12/808,325, filed Jun. 17, 2010, now U.S. Pat. No. 8,304,242, which is a U.S. National Stage Filing under 35 U.S.C. 371 from International Patent Application Serial No. PCT/US2008/087207, filed Dec. 17, 2008, which claims priority to U.S. Provisional Application Ser. No. 61/014,396, filed Dec. 17, 2007, the disclosures of which are incorporated herein by reference in their entirety.

FIELD OF THE INVENTION

The invention relates to methods for detecting surface defects in coated substrates (e.g., inorganic-coated polymer surfaces) and, more specifically, to the use of hydrophobic fluorescent materials to detect surface defects.

DESCRIPTION OF RELATED ART

Polymers are commonly used materials because of their flexibility, light weight, and low cost. Many polymer properties could be enhanced by the addition of an inorganic coating on their surface. This inorganic film could serve as a gas diffusion barrier for various packaging applications. The inorganic layer could also serve to protect the underlying polymer and give the polymer higher strength. Unfortunately, inorganic layers are difficult to deposit on polymers because the deposition of inorganic materials is usually performed at temperatures above the melting temperature of the polymer.

Alumina-coated polymer surfaces are widely used in industrial and consumer products. Atomic layer deposition ("ALD", sometimes alternatively referred to as chemical vapor deposition "CLD") is used to deposit a thin nanometer layer of alumina or other inorganic or metallic materials onto a polymer surface. ALD coatings can be used to insulate, facilitate charge dissipation and functionalize the surface of MEMS (Micro-Electro-Mechanical Systems) devices. Polyimides are commonly used as the polymer. Materials such as alumina-coated polyimides are used in the semiconductor industry to prepare high vacuum, vapor resistant sealing packages for semiconductor wafers.

Due to inherent limitations and variability in atomic layer deposition, various defects such as non-coated areas, surface irregularities, cracks, or scratches can be introduced during large scale production. These defects can be introduced during the deposition of the inorganic layer, or afterwards during further processing or handling.

Several quality control testing procedures exist, but tend to be costly, time consuming, and expensive. One example is a helium leakage test. This test measures the vapor transmission rate through the polymer as an indicator of the integrity of the inorganic coating. This test can indicate the presence of a defect, but does not allow detection of the exact location of the defect.

Other tests for water vapor permeation include gravimetric (loss of water or gain of water on $P_2O_5$), capacitive or resistive (using a humidity sensor), spectroscopy, calcium degradation (either optical or change in resistance), and radioactive (using tritium or $^{14}CO$).

A publication described a method for detecting under-film corrosion using a hand-held UV lamp (D. E. Bryant and D. Greenfield, *Progress in Organic Coatings*, 57(4): 416-420 (2006)). The chemical 8-hydroxyquinoline-5-sulfonic acid hydrate was used to study corrosion of coated aluminum, and 9-anthyl-5-(2-nitrobenzoic acid)disulfide was used with iron. Metals coated with various polymers were scored with a scalpel, allowing corrosion to occur.

Atomic force microscopy ("AFM") was used to examine surface cracks on an indium tin oxide coated polycarbonate substrate that had been subjected to cycles of bending (L Ke et al., *Applied Physics A: Materials Science & Processing*, 81(5): 969-974 (2005)). AFM showed that bending increases the roughness of the inorganic coating surface. Calcium degradation test showed that surface cracks are perpendicular to the flexing direction, and that barrier performance deteriorated after bending. An organic light emitting device ("OLED" or "organic LED") fabricated on the surface showed decreased electrical and optical performance due to moisture and oxygen permeation.

An auto-optical inspection system ("AOI") for detection of defects in OLEDs was described by D. B. Perng et al., *Journal of Physics: Conference Series*, 13: 353-356 (2005). The publication indicated that OLED defects commonly include dark points, non-uniform luminescence, surface scratches, insufficient rubber widths, and lack of color uniformity. The computer-controlled AOI is based on a lighting mechanism including a conducting fixture, a UV light, a coaxial LED light, and a back light.

Various U.S. patents have issued offering methods for detecting surface defects of materials.

U.S. Pat. No. 4,968,892 (issued Nov. 6, 1990) describes a testing apparatus for identifying surface defects in a workpiece. The piece is treated with a fluorescent substance that is trapped in flaws in the surface. The apparatus includes a light source, lenses, and filter to scan the surface.

U.S. Pat. No. 5,723,976 (issued Mar. 3, 1998) describes a method for detecting defects in encapsulated electronic components. The method involves immersing the component in an aqueous florescent solution of a water-soluble fluorescent substance that fluoresces when moistened, but that does not fluoresce when dry. The component is visualized in humid air, and then in dry air to detect fluorescence (when moist) and lack of fluorescence (when dry) at a defect.

U.S. Pat. No. 5,965,446 (issued Oct. 12, 1999) suggests a method of detecting defects in surfaces. A solution of fluorescent molecules in a volatile organic solvent is prepared, and applied across the surface using a slip of paper. The paper is used to uniformly distribute the solution across the surface before the organic solvent evaporates.

U.S. Pat. No. 6,097,784 (issued Aug. 1, 2000) offers a method for amplifying defects connected to a top surface of a semiconductor device. A dye is applied to the top surface, and leeched into a developing gel. The gel develops defect indications that are more easily visualized than the defects themselves. The dye can be a fluorescent dye.

U.S. Pat. No. 6,427,544 (issued Aug. 6, 2002) suggests an environmentally friendly method for detecting defects in parts. The parts are submerged in a mixture of a penetrant dye and supercritical carbon dioxide. The part is removed, and inspected for the presence of dye in any defects. The dye can be a fluorescing penetrant dye that is visualized with UV light.

U.S. Pat. No. 6,677,584 (issued Jan. 14, 2004) offers a manufacturing fluid containing a fluorescent dye. A component is either ground or cut in the presence of the manufacturing fluid, and the component is subsequently inspected for surface cracks or defects. The manufacturing fluid can be especially useful in processing of ceramic parts.

U.S. Pat. No. 6,916,221 (issued Jul. 12, 2005) describes an optical method for determining defects in OLEDs. A digital image of the excited OLED surface is obtained, and a computer or user inspects the image to determine defects.

U.S. Pat. No. 6,943,902 (issued Sep. 13, 2005) describes a method of determining layer thickness or respective amount of filling, layer thickness distribution, defect, accumulation or inhomogeneity within a material layer. The material is mixed with an agent that absorbs radiation before the layer is prepared. The layer is irradiated, and the emitted light is detected. In this method, the agent is permanently embedded throughout the layer.

While inorganic-coated polymers are widely used in industry, surface defects degrade, and potentially eliminate, the desirable properties of the materials. For example, a defect may allow water to penetrate the material, or may reduce the ability of the material to hold a vacuum. Thus, despite efforts made to date, simple, reliable methods to verify the integrity of materials, or conversely, simple, reliable methods to detect surface defects of materials are still needed. Additionally, methods that provide detection of the location of the defects are desirable.

SUMMARY OF THE INVENTION

Surface defects in materials having a polymer layer coated with a hydrophilic layer (e.g., a surface layer of an inorganic substance) can be detected and localized using at least one lipophilic fluorescent substance. Contacting the material with the fluorescent substance renders any surface defects fluorescent, while the remaining surface lacking defects is not labeled.

In one aspect, a method is provided for identifying a defect in a surface. The method involves a) providing a substrate having a hydrophobic surface at least partially coated by a hydrophilic layer, wherein the hydrophilic layer has the defect therein; b) contacting the substrate with a lipophilic, fluorescent substance, for a sufficient amount of time for the substance to contact the defect; c) exciting the fluorescent substance with energy at an appropriate wavelength to generate a detectable fluorescence response; and d) detecting the fluorescence response of the substance. The method can further include washing the substrate after contacting the substrate with the lipophilic, fluorescent substance. The substrate can include a polymer. The hydrophilic layer can be or include an inorganic material (e.g., a metal oxide). The hydrophilic layer is typically less than 10 Å in thickness. The lipophilic, fluorescent substance can be a fluorescent compound that includes a 4,4-difluoro-4-bora-3a,4a-diaza-s-indacene moiety. The lipophilic, fluorescent substance can further include a lipophilic moiety or can include two or more lipophilic moieties. For example, the lipophilic moiety can be a hydrocarbon having 1-20 carbon atoms, such as an alkyl group having 1-20 carbon atoms or a phenyl or styryl group. The lipophilic, fluorescent substance can be associated with a microparticle or a semiconductor nanocrystal.

In another aspect, a lipophilic, fluorescent substance is provided that includes a 4,4-difluoro-4-bora-3a,4a-diaza-s-indacene moiety and a lipophilic moiety. The lipophilic moiety can be a hydrocarbon having 1-20 carbon atoms, such as an an alkyl group having 1-20 carbon atoms or a phenyl or styryl group. The lipophilic, fluorescent substance can be associated with a microparticle.

In yet another aspect, a substrate is provided that includes an identifiable defect. The substrate can include a hydrophobic surface that is at least partially coated by a hydrophilic layer (e.g., an inorganic material) in which there is a defect. A lipophilic, fluorescent substance can be in contact with the defect. Any lipophilic, fluorescent substance can be in contact with the defect, including, for example, a substance that includes a 4,4-difluoro-4-bora-3a,4a-diaza-s-indacene moiety and a lipophilic moiety.

In yet another aspect, kits are provided including a lipophilic, fluorescent substance and, optionally, additional components for carrying out the disclosed methods.

The compositions, kits, and methods provided herein offer numerous advantageous over traditional approaches for visualizing surface defects and provide an inexpensive, rapid, and relatively easy to use alternative to existing approaches.

DETAILED DESCRIPTION OF THE INVENTION

Figure 1:
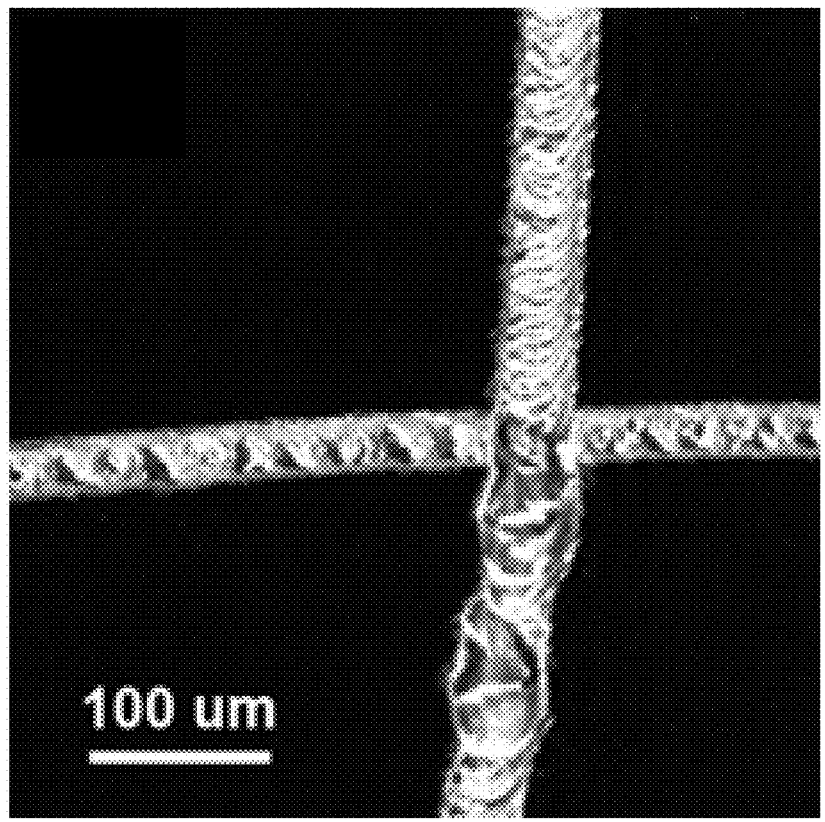
FIG. 1 is an image demonstrating that lipophilic, fluorescent molecules adhere selectively to scratches introduced in an ALD alumina coating.

Before describing the present invention in detail, it is to be understood that this invention is not limited to specific compositions or process steps. It should be noted that, as used in this specification and the appended claims, the singular form "a", "an" and "the" include plural references unless the context clearly dictates otherwise. It also should be noted that the term "about", when used to describe a numerical value, shall encompass a range up to ±15% of that numerical value, unless the context clearly dictates otherwise. While compositions and methods are described in terms of "comprising" various components or steps (interpreted as meaning "including, but not limited to"), the compositions and methods can also "consist essentially of" or "consist of" the various components and steps, such terminology should be interpreted as defining essentially closed-member groups.

Compositions and Methods of Use

Methods are provided for the detection of defects in a material. One embodiment of the invention is directed towards methods for the detection of surface defects in a material. The material can comprise, for example, a polymer layer coated with an inorganic layer. The method can comprise contacting the material with at least one lipophilic fluorescent substance to allow the substance to localize at the defect, and detecting the localized substance. The method can be used to detect various types of surface defects, including, without limitation, mechanical defects, such as cracks, pin holes, surface irregularities, scratches, uncoated areas, flaking, or any other type of defect that can arise during production or handling of the material. Also provided are methods for detecting the presence of surface particles or contaminants (e.g., grease, oil, dust, fibers, and the like). The present methods can be used for detecting defects that traverse the full thickness of a surface layer on a substrate. For example, a crack or pin hole in a hydrophilic coating that leaves a portion of an underlying hydrophobic substrate exposed can be detected using the subject lipophilic fluorescent substances. The disclosed fluorescent substances can label surface defects ranging in size from several to hundreds of nanometers to microns or larger. For example, defects can be identified having a width or diameter (e.g., in the case of a pinhole defect) of about 500 nm or less; or about 250 nm or less; or about 100 nm or less; or 50 nm or less.

The material can generally be any material. Examples of materials include OLEDs (organic light-emitting diodes), thermal ground planes, solar panels, films and bags (such as those used the electronics, food packaging, or medical device industries), fiber optics, flexible displays, liquid crystal display (LCD) assemblies, flat panel displays, magnetic information storage media (MIS), Micro-Electro-Mechanical System (MEMS), and Ultra large-scale integration (ULSI) circuits.

The material can include a polymer or a combination of polymers. The polymer can be in the form of a surface layer. The polymer or polymer layer can generally be any polymer. The polymer is preferably hydrophobic. Examples of polymers include polystyrene, polyurethane, polyimide, epoxy, polyethersulfon (PES), polyethylene naphthalate (PEN), HSPEN (heat stabilized polyethylene naphthalate), KAPTON (a polyimide membrane commercially available from DuPont), polyetheretherketone (PEEK), polysulfone (PSF), polyetherimide, polyethylene phthalate, and polyethylene terephthalate (PET). The polymer can generally be in any three-dimensional configuration. Examples of configurations include planar sheets, films, coatings, tubing, fibers, and beads.

The material (e.g., a substrate formed of a polymer) can further include at least one layer of a coating. The coating can be a continuous coating (e.g., a film) or can cover only a portion of the substrate. The coating can include any type of material (e.g., a polymer or an inorganic material), so long as it is less hydrophobic than the substrate material. For example, the coating can be a hydrophilic material (e.g., a hydrophilic polymer or an inorganic material). In certain embodiments, the coating is an inorganic layer. The inorganic layer can generally be any inorganic layer. The inorganic layer is preferably hydrophilic. Inorganic layers can be metal oxide layers. Inorganic layers can be metal-anion solids such as ZnS, GaP, $Ta_2O_3$, $Al_2O_3$ (alumina), $TiO_2$, $GeO_2$, and $VO_x$. The coating can range in thickness. For example, the coatings can be less than about 1 micron; or less than about 500 nm; or less than about 100 nm; or less than about 50 nm. The coating can be applied or deposited onto a substrate by any means known used in the art. In certain embodiments, an inorganic coating layer is applied by atomic layer deposition (ALD) to form a film on the substrate having a thickness of 50 nm or less (e.g., about 25 nm).

The lipophilic fluorescent substance can generally be any lipophilic fluorescent substance. Examples of lipophilic fluorescent substances include fluorescent dyes, fluorescent microspheres, and quantum dots (sometimes referred to as semiconductor nanocrystals). The fluorescent substance can generate fluorescence prior to application to the sample or can generate fluorescence during use (e.g., upon contact with the sample). For example, lipophilic, fluorescent substances can appear non-fluorescent or minimally fluorescent when dissolved in an aqueous solution, such as water or a buffer. However, when in a hydrophobic environment (e.g., when in contact with a hydrophobic surface), certain lipophilic fluorescent substances (e.g., diaza-indacenes, squarenes and some styryl dyes) can produce an intense fluorescence signal.

The type of lipophilic fluorescent substance used in the present methods can vary depending on, for example, the composition and configuration of substrate and coating, the thickness of the coating, and the type and size of defect. Lipophilic fluorescent substances are generally of a size that permits ready entry into nanometer-scale defects. Certain substances provided herein are relatively small molecules (e.g., molecular weight of about 200-400). However, larger fluorescent substances with dimensions in the nanometer or micron range may be desirable for detecting larger defects. Lipophilic fluorescent substances are typically hydrophobic compounds or substances that tend to be non-polar and are not considered water soluble. Lipophilic substances tend to dissolve in non-polar solvents, such as, methylene chloride, isopropanol, ethanol, hexane, and the like, and have no affinity or a negligible affinity for hydrophilic surfaces. The fluorescent substance itself may be lipophilic. Alternatively, the fluorescent substance includes a fluorescent moiety and a lipophilic moiety (e.g., a lipophilic pendant group). Certain fluorescent moieties can be lipophilic. In certain embodiments, the fluorescent moiety is relatively less lipophilic than the lipophilic moiety. Certain fluorescent moieties can be hydrophilic. A fluorescent substance having a fluorescent moiety that is relatively less hydrophobic than the pendant moiety can be used when it is desired that the substance orient itself relative to the surface. For example, when deposited onto a hydrophobic surface, a lipophilic pendant group can adhere to the surface (e.g., by hydrophobic interactions), while the relatively less hydrophobic fluorescent moiety can present itself away from the surface. The lipophilic moiety can be bonded (e.g., covalently bonded) to a fluorescent molecule and can further include a spacer that can distance the lipophilic moiety from the fluorescent moiety. In certain embodiments, the fluorescent molecule can include more than one pendant group, where the pendant groups can be the same or different. For example, the compound can include 2 or 3 or 4 or more lipophilic groups, which can be the same or different. Lipophilic groups are typically chosen so as not to interfere with the fluorescence properties of the fluorescent molecule. Any type of lipophilic or hydrophobic group can be used in the preparation of lipophilic, fluorescent substances and are well known to those skilled in the art. A representative class of lipophilic moieties includes hydrocarbons. Hydrocarbons can be saturated or unsaturated, linear, branched, or cyclic, and can include aliphatic, and/or aromatic moieties. Certain hydrocarbons include a conjugated hydrocarbon chain. Exemplary lipophilic hydrocarbon moieties include alkyl groups having 1-20 carbon atoms. For example, the lipophilic moiety can be a saturated alkyl group having 10 or less carbon atoms (e.g., 1 to 3; or 3 to 5; or 5 to 7; or 7 to 9; or 10), which can be substituted or unsubstituted (e.g., methyl, ethyl, propyl, butyl, and the like). Alternatively, the lipophilic moiety can be an unsaturated hydrocarbon, which can be substituted or unsubstituted, or a conjugated hydrocarbon with alternating single and double bonds. Other exemplary lipophilic moieties are or include an aromatic moiety, such as phenyl or styryl. Other classes of lipophilic moieties include compounds that contain a heteroatom, such as N, S, O, or a halogen. Yet other classes of lipophilic substances include fatty acids, fatty sulfonic acids or fatty sulfates (such as sodium dodecyl sulfate). In certain embodiments, the fluorescent substance is substituted with 2 to 4 or more lipophilic pendant groups, which can be the same or different. For example a fluorescent substance can be substituted with 2 or 3 or 4 alkyl groups, where each alkyl group has 1-20 carbon atoms (e.g., methyl, ethyl, propyl, butyl, and the like). In other embodiments, the fluorescent substance is substituted with more than one type of lipophilic group. For example, a fluorescent substance can be substituted with a combination of moieties, such as, for example hydrocarbon moieties (e.g., linear or branched alkyl, phenyl, styryl, or the like).

Examples of lipophilic fluorescent substances include fluorescent dyes, fluorescent microspheres or microparticles, and quantum dots (sometimes referred to as semiconductor nanocrystals). Any type of fluorescent dye may be used in the practice of the described methods. In certain embodiments, the fluorescent dye can absorb or emit radiation in the visible range of the electromagnetic spectrum. Alternatively, the fluorescent dye can absorb or emit radiation in the near IR region of the spectrum. Near IR dyes can be effectively used to visualize defects in substrates that generate background fluorescence. Many fluorescent compounds tend to lose fluorescence emission intensity (referred to as "photobleaching") upon sustained illumination (e.g., from seconds to longer exposure times). Photobleaching arises for various reasons, including, for example, irreversible modification of the dye structure. Lipophilic, fluorescent substances are provided that resist photobleaching and are, therefore, well-suited for use in detection and characterization of defects according to the methods provided herein.

Loss of fluorescence emission intensity also can occur when a fluorescent substance is present in a high concentration or agglomerates. Thus, it is generally desired to use a lipophilic fluorescent compound in the practice of the disclosed methods that exhibits minimal or no loss in fluorescence emission intensity when present at a high concentration (e.g., when localized in or on a defect), or exhibits a loss in intensity or at a rate that is slower than the time scale of the detection period (such that the loss in intensity does not affect the measurement). Provided herein are fluorescent substances that are sufficiently lipophilic to adhere to hydrophobic substrates (e.g., polymers) and yet maintain their fluorescence emission intensity when deposited in or on a surface defect. In contrast to many fluorescent compounds, it has been found that certain lipophilic, fluorescent compounds provided herein (e.g., BODIPY dyes) actually exhibit an increase in fluorescence signal intensity when present in high concentration. Particular dyes, wherein the dye is hydrophobic, provided herein (e.g., BODIPY) maintain or increase fluorescence signal intensity when used to detect surface defects. This unique attribute is particularly advantageous in the imaging of micron or nanometer sized defects containing minute quantities of the fluorescent material. Although not necessary for the practice of the described methods, particular lipophilic, fluorescent compounds provided herein also can exhibit a shift in emission wavelength (e.g., red-shift) when localized within a defect. Compounds that exhibit a spectral shift towards longer wavelengths can be used, for example, to visualize defects in substrates that produce background fluorescence.

One representative class of hydrophobic fluorescent dyes that is suitable for detecting surface defects includes compounds having a boron dipyrromethene (abbreviated as BODIPY) core structure (e.g., compounds having a 4,4-difluoro-4-bora-3a,4a-diaza-s-indacene core). BODIPY-based compounds can be substituted with one or more lipophilic pendant groups, as described herein. Particular examples of BODIPY-based fluorescent compounds that can be utilized in the described methods include those substituted with, for example, a hydrocarbon, such as methyl, propyl, phenyl, or styryl. For example, representative BODIPY compounds include, 1,3,5,7,8-pentamethyl BODIPY and 1,3-di-n-propyl BODIPY.

Other examples of BODIPY-based fluorescent compounds that can be utilized in the described methods include 4,4-difluoro-1,3,5,7,8-pentamethyl-4-bora-3a,4a-diaza-s-indacene; 4,4-difluoro-1,3-dimethyl-5,7-diphenyl-4-bora-3a,4a-diaza-s-indacene; 4,4-difluoro-1,3,5,7-tetraphenyl-4-bora-3a,4a,8-triaza-s-indacene; 4,4-difluoro-1,3-diphenyl-5-(2-pyrrolyl)-4-bora-3a,4a-diaza-s-indacene; 4,4-difluoro-1,3-dipropyl-4-bora-3a,4a-diaza-s-indacene; 4,4-difluoro-1,3,5,7-tetramethyl-4-bora-3a,4a-diaza-s-indacene, 4,4-difluoro-1,3-diphenyl-5,7-dipropyl-4-bora-3a,4a-diaza-s-indacene; 4,4-difluoro-1-phenyl-3-(4-methoxyphenyl)-5-(2-pyrrolyl)-4-bora-3a,4a-diaza-s-indacene; difluoro(1-((3-(4-methoxyphenyl)-2H-isoindol-1-yl)methylene)-3-(4-methoxyphenyl)-1H-isoindolato-$N^1,N^2$)boron; difluoro(5-methoxy-1-((5-methoxy-3-(4-methoxyphenyl)-2H-isoindol-1-yl)methylene)-3-(4-methoxyphenyl)-1H-isoindolato-$N^1,N^2$)boron; 4,4-difluoro-2-ethyl-1,3,5,7,8-pentamethyl-4-bora-3a,4a-diaza-s-indacene; 4,4-difluoro-1,3-dimethyl-5-styryl-4-bora-3a,4a-diaza-s-indacene; 4,4-difluoro-3,5-di(4-methoxyphenyl)-4-bora-3a,4a-diaza-s-indacene; 3-decyl-4,4-difluoro-5-styryl-4-bora-3a,4a-diaza-s-indacene; 4,4-difluoro-1,3-dimethyl-5-(4-methoxyphenyl)-4-bora-3a,4a-diaza-s-indacene; 4,4-difluoro-1,3-dimethyl-5-(2-thienyl)-4-bora-3a,4a-diaza-s-indacene; difluoro(1-((3-(2-(5-hexyl)thienyl)-2H-isoindol-1-yl)methylene)-3-(2-(5-hexyl)thienyl)-1H-isoindolato-$N^1,N^2$)boron; 4,4-difluoro-1,3,5,7-tetraphenyl-4-bora-3a,4a-diaza-s-indacene; 4,4-difluoro-1,3-dimethyl-5-(2-(5-methoxycarbonyl-4-methyl-2-oxazolyl)ethen yl)-4-bora-3a,4a-diaza-sindacene; and difluoro(5-methoxy-1-((5-methoxy-3-(2-(5-(4-methoxyphenyl))thienyl)-2H-isoindol-1-yl)methylene)-3-(2-(5-(4-methoxyphenyl))thienyl)-1H-isoindolato-$N^1,N^2$)boron.

Yet other examples of hydrophobic fluorescent dyes that can be used in the practice of the described methods include p-aminophenyl phosphorylcholine, naphthalenes, anthracenes, phenanthrenes, indoles, carbazoles, stilbenes, benzimidazoles, benzoxazoles, benzothiazoles, quinolines, benzoxanthrones, oxazoles, isoxazoles, oxadiazoles, benzofurans, pyrenes, perylenes, coronenes, coumarins, carbostyryls, bimanes, acridines, polyphenylenes such as terphenyl, alkenyl and polyalkenyl dyes (including 1,6-diphenyl-1,3,5-hexatriene and 1,1,4,4-tetraphenyl-1,3-butadiene).

Other long wavelength dyes such as luminescent phenoxazones, oxazines and pyronines (including nile red); porphines, porphyrins, phthallocyanines and their metallated complexes, including complexes with rare earth ions such $Eu^{3+}$ and $Tb^{3+}$; xanthenes (including fluoresceins and rhodamines); cyanine, carbocyanines and merocyanines (including styryl dyes; hydrocarbon derivatives such as rubrenes and azulenes; are suitable provided that they are either electrically neutral; or their ionic charges are balanced by lipophilic counterions that include but are not limited to lipophilic ammonium salts (such as hexadecyltrimethylammonium or benzyltrimethylammonium), fatty acids, fatty sulfonic acids or fatty sulfates (such as sodium dodecyl sulfate), detergents such as anionic or cationic derivatives of cholic acids, tetraarylphosphonium or tetraarylboride; or they contain a suitable functional group (as described above) for copolymerization.

The fluorescent lipophilic substance may be contained within or on a microparticle (e.g., a spherical particle). Microparticles include those sized so as to be able to readily enter a defect (e.g., a crack or pinhole) in a surface. In certain embodiments, the fluorescent lipophilic substance is contained within or on a microparticle having low surface charge (e.g., particles with lipophilic surfaces). Microparticles can generally have any shape or size. For example, microparticles can be sized to have a dimension along the longest axis that can be about 5 nm to about 20 µm. Certain microparticles can be spherical (referred to as microspheres). The spherical microspheres can generally have any diameter. Generally, the diameter (or length across the longest dimension, in the case of non-spherical particles) can be about 5 nm to about 20 µm. Presently preferred diameters are about 10 µm to about 100 nm. Specific examples of diameters include about 5 nm, about 6 nm, about 7 nm, about 8 nm, about 9 nm, about 10 nm, about 11 nm, about 12 nm, about 13 nm, about 14 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, about 30 nm, about 40 nm, about 50 nm, about 60 nm, about 70 nm, about 80 nm, about 90 nm, about 100 nm, about 200 nm, about 300 nm, about 400 nm, about 500 nm, about 600 nm, about 700 nm, about 800 nm, about 900 nm, about 1 µm, about 2 µm, about 3 µm, about 4 µm, about 5 µm, about 6 µm, about 10 µm, about 20 µm, about 30 µm, about 1 µm, about 2 µm, about 3 µm, about 4 µm, about 10 µm, about 20 µm and ranges between any two of these values. In certain embodiments, particles of less than 1 micron; or less than 500 nm; or less than 100 nm are suitable for use in methods to visualize micron to nanometer-sized defects.

The spherical microspheres can be prepared from generally any material. It is presently preferred that the spherical standards are prepared from a polymer material. Example polymer materials include polymers and copolymers of styrenes and divinyl benzenes; an acrylate or methacrylate ester; an acrylic acid or methacrylic acid; an acrylamide or methacrylamino; an acrylonitrile or methacrylonitrile; vinyl and vinylidene halides, esters and ethers; alkenes, including ethylene, propylene, butadiene and isoprene; epoxides and urethanes.

The spherical microspheres can be stained with at least one fluorescent compound, such as the dyes described above. The one or more fluorescent dyes in the spherical microspheres can be selected to match the excitation source (e.g., a laser such as an argon-ion laser, a krypton-argon laser, or a helium-neon laser, a LED, UV lamp, etc.), and/or an optical filter commonly used in scanner, fluorescence microscopes or confocal laser-scanning microscopes. For example, certain microspheres for use according to the described methods have diameters of about 10 nm or less and low surface charge loaded with a fluorescent dye that emits fluorescence in the green region of the electromagnetic spectrum.

The lipophilic, fluorescent substance can be a quantum dot (also referred to as a "semiconductor nanocrystal" or "nanocrystal"). Quantum dots are nanometer-scale atom clusters formed of a core (typically zinc sulfide), a semiconductor shell, and coating. A lipophilic moiety can be attached to the polymer coating or directly to the semiconductor shell to create nanocrystals that meet specific defect detection requirements and to minimize non-specific attachment of the quantum dot to the surface. The surface of the quantum dots can be relatively hydrophobic, and can interact with un-coated (defect of ALD deposition) polymer (e.g., membrane) surfaces by hydrophobic interactions and lead to defect detection. Typically, quantum dots can be excited with shorter wavelength excitation sources such as UV or violet laser and can emit at wavelengths in the visible region to the near infrared region of the electromagnetic spectrum (e.g., at about 500 to about 800 nm). Quantum dots can produce a bright fluorescence signal and are typically more photostable and less susceptible to bleaching than traditional organic fluorophores, even under high power excitation over extended periods of time (e.g., up to several hours). Further, quantum dots do not generally exhibit a marked reduction in fluorescence emission intensity when accumulated at higher concentration. As was discussed with reference to certain classes of lipophilic fluorescent dyes, quantum dots that maintain fluorescence emission intensity during use are generally desirable for use in visualization of surface defects. Quantum dots can generally be any color quantum dot. Examples of currently commercially available quantum dots suitable for use in the disclosed methods include the QDOT nanocrystal products, such as QDOT 525 nanocrystals, QDOT 545 nanocrystals, QDOT 565 nanocrystals, QDOT 585 nanocrystals, QDOT 605 nanocrystals, QDOT 625 nanocrystals, QDOT 655 nanocrystals, QDOT 705 nanocrystals, and QDOT 800 nanocrystals, all available from Invitrogen Corporation (Carlsbad, Calif.).

The lipophilic fluorescent substance can be directly applied to the material to be analyzed. Alternatively, the fluorescent substance can be present in a liquid solution or suspension. For example, the liquid or suspension can comprise water and an organic solvent, such as DMSO, DMF, toluene, alcohol (such as methanol, ethanol, or 2-propanol), methylene chloride, and the like, or mixtures thereof.

Methods are provided for identifying a defect in or on coated substrate using a lipophilic fluorescent substance. A surface of the substrate can be coated in its entirety, or only a portion of the surface can be coated with a coating. In one method, a hydrophobic polymer substrate coated with a hydrophilic coating, such as alumina, is treated with a solution of a lipophilic fluorescent substance. The fluorescent molecule or material can selectively bind to defect sites, based on the surface adhesion characteristics of the system. The contacting step can generally comprise any suitable application method, such as dipping the material into a liquid solution or suspension, spraying a liquid solution or suspension onto the material, spraying the lipophilic fluorescent substance directly onto the material, rolling the fluorescent substance directly onto the material, or combinations thereof. The lipophilic substance can contact the defect (e.g., crack) and adhere to the underlying polymer substrate left exposed by the defect. Lipophilic substances are provided that can easily enter into nanometer-scale defects, such as typically found, for example, in ALD barrier coatings. The lipophilic substance can adhere to the hydrophobic substrate via any type of non-covalent interaction (e.g., hydrophobic bonding) by virtue of its hydrophobicity. Further, the lipophilic substance has little or no affinity for the hydrophilic surface coating and can be readily removed from the hydrophilic surface.

The method can further comprise washing the material after the contacting step and before the detecting step to remove any non-localized substance. The washing step can be performed once, or multiple times.

The detecting step can qualitatively detect the presence or absence of localized lipophilic fluorescent substance, or can quantitatively detect the amount of localized lipophilic fluorescent substance. The detecting step can also determine the location of the localized lipophilic fluorescent substance on the material. The detecting step can comprise applying radiation to the material in order to detect fluorescence emitted from the localized lipophilic fluorescent substance. The particular type and wavelength of radiation is selected based upon the spectral characteristics of the fluorescent substance, and is well within the talents of the skilled artisan. Examples and sources of radiation include UV light, lasers, LED light, and visible light. The detecting step can further comprise preparing an image of the material. The image can be a film image or an electronic image. Depending on the size of the defect, a microscope may be useful in detecting and preparing an image of the defect. The fluorescence emission of the localized lipophilic fluorescent substance allows direct identification and localization of defects. The methods can be used to visualize defects in many types of materials and can be applied, for example, for the development and manufacturing of thin film gas diffusion barriers for the organic light-emitting diodes (OLEDs), photovoltaic (PV), and liquid crystal display (LCD) industries as well as the packaging of: medical devices, sensor skins, electronic circuits, micro-, and nano-systems.

Kits

An additional embodiment of the invention is directed towards kits useful for the detection of surface defects in a material. The kits can comprise at least one lipophilic fluorescent substance (e.g., dyes, fluorescent microspheres, or quantum dots) as described above. The kits can comprise instructions for performing the above described methods. The kits can comprise a "positive control" material containing at least one surface defect. The kits can comprise a "negative control" material that does not contain surface defects. The kits can comprise a wash material useful for removing non-localized fluorescent substance from the material.

The following examples are included to demonstrate preferred embodiments of the invention. It should be appreciated by those of skill in the art that the techniques disclosed in the examples which follow represent techniques discovered by the inventor(s) to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

Binding of Lipophilic Fluorescent Materials to Polymers

A piece of 2 cm×2 cm sized thin polyethylene terephthalate (PET) plastic film coated on one side with alumina About 3 mm-wide edge on the lift side of the film is not coated. The film was immersed in to a solution of 1,3-dimethyl-5-styryl BODIPY (Invitrogen Corp., Carlsbad, Calif.; 0.04 mg/mL in 70% ethanol, 30% deionized water (v/v) for 3 minutes. The film was removed and washed with 70% ethanol (v/v) three times and examined with a Nikon fluorescence microscope with a 550 nm excitation/570 nm emission filter set. The uncoated edge of polymer membrane became red fluorescent; the alumina coating was not stained.

Example 2

Detection of Surface Defects Using Dyes

An equilateral triangle-shaped scratch (about 1 mm×1 mm×1 mm; the scratch lines had a width of about 0.1 mm) was made on a piece of alumina coated thin polyethylene terephthalate (PET) plastic film to mimic a coating defect. The film was immersed in to a solution of 1,3-di-n-propyl BODIPY (Invitrogen Corp., Carlsbad, Calif.; 0.04 mg/mL in 70% ethanol, 30% deionized water) for 2 minutes. The film was removed and washed with 70% (v/v) ethanol three times and examined using a Nikon fluorescence microscope using a standard FITC filter set (490 nm excitation/515 nm emission). The scratch became green fluorescent based on the deepness of the damage. The remaining unscratched alumina coating was not stained. This result indicated that the defect in a large alumina coated film can be 1) labeled with fluorescent dye, 2) easily detected and 3) easily located.

Example 3

Detection of Surface Defects Using Fluorescent Microspheres

Several scratches (about 2 mm long and 0.02 mm wide) were made by scratching a piece of alumina-coated thin polyethylene terephthalate (PET) membrane with a sharp 22 gauge syringe needle to mimic a defect.

A suspension of 20 nm green fluorescent microspheres (emission maximum at 515 nm) with low surface charge was prepared by adding 2% microsphere stock to a 50% ethanol, 50% deionized water mixture (v/v) for a final concentration of 0.5% microsphere.

The membrane sample was immersed into the microsphere suspension for 3 minutes at room temperature. The film was removed and washed with 50% ethanol (v/v) three times. The membrane was allowed to dry in air, and was examined using a Nikon fluorescence microscope with a FITC filter set (excitation: 490 nm/emission: 515 nm). The scratches became bright green fluorescent, and were easily visualized and localized on the membrane.

Example 4

Detection of Surface Defects Using Dually Fluorescent Microspheres

Several scratches (about 2 mm long and 0.02 mm wide) were made by scratching a piece of alumina-coated thin polyethylene terephthalate (PET) membrane with a sharp 22 gauge syringe needle to mimic a defect.

A suspension of 110 nm dual emission microspheres (emission max at 565 nm and 755 nm) with low surface charge was prepared by adding 5% microsphere stock to a 50% ethanol, 50% deionized water mixture (v/v) for a final concentration of 0.5% microsphere.

The membrane sample was immersed into the microsphere suspension for 3 minutes at room temperature. The film was removed and washed with 50% ethanol (v/v) three times. The membrane was allowed to dry in air, and was examined using a Nikon fluorescence microscope with a XF101 filter set (excitation: 543 nm/emission: 565 nm) and a XF48-2 filter set (excitation: 635±25 nm/emission: 725 nm long pass). The scratches became orange fluorescent when examined under the XF101 filter, and became red fluorescent when examined under the XF48-2 filter set.

Example 5

Visualization of Mechanical Cracks

Mechanical cracks were visualized using a diaza-indacene fluorophore with hydrophobic substituents. 25 nm thick ALD alumina barrier films were deposited onto polyethylene naphthalate (PEN) substrates (Teonex Q65, Dupont Teijin, Inc.). The coated specimens, some of which were mechanically manipulated in order to intentionally generate defects, were then soaked in a fluorescent tag solution for 5 min. Solvent solution containing 70% ethanol and 30% water was used to wash away excess tag molecules not attached to the film. The sample was then dried using clean dry air and maintained in an ultraviolet-safe environment. A LSM 510 confocal microscope (Carl Zeiss, Inc.) was used for inspection of the tagged sample. A 488 nm Argon 12 laser source was used to excite the tags and the fluorescent emission (maximum at 515 nm) was measured with a 505-530 nm band pass filter. A PEN substrate with no coating, a PEN substrate with an ALD alumina coating, and an identically coated PEN substrate bearing intentionally-made scratches were compared. The tag molecule attached well to the bare PEN film, yielding a bright field across the whole sample, whereas an all dark field image revealed that the tag did not attach to the ALD alumina (data not shown). FIG. 1 shows that the fluorescent molecule selectively attached only to the hydrophobic PEN substrate, where it is exposed by the scratch in the hydrophilic ALD alumina coating.

Example 6

Visualization of Mechanical "Channel Cracks"

Figure 2:
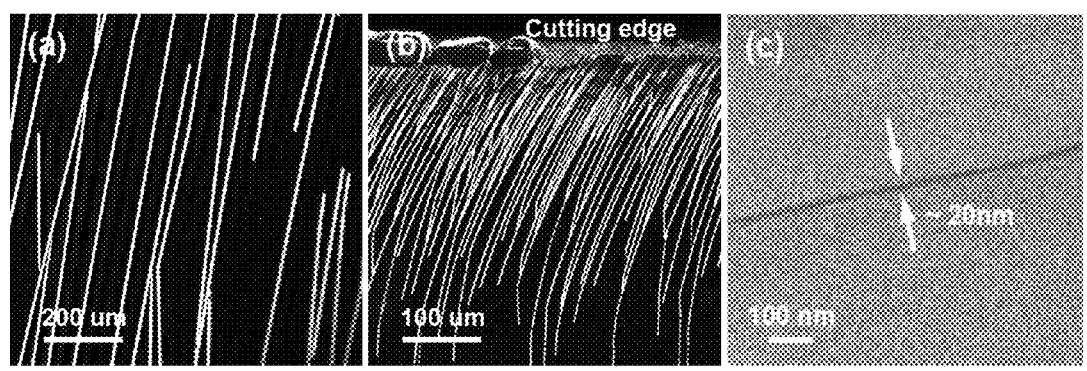
FIG. 2 shows images of cracks in an ALD alumina coating rendered visible by a lipophilic, fluorescent substance: (A) series of channel cracks generated at the specimen's interior after a 5% externally applied strain, (B) cracks at edge of specimen resulting from shearing during sample preparation, (C) FESEM image demonstrating the true size of a single shear crack.

The failure mode of "channel cracking" is commonly encountered when a brittle inorganic coating is subjected to mechanical strain or thermal cycling. However, a series of such cracks is not readily observed in transparent films. To demonstrate the use of lipophilic fluorescent tags, an external tensile loading was applied to PEN substrates coated with 25 nm of ALD alumina. The fluorescent tags were then applied to these specimens according the procedure described in Example 5. FIG. 2 shows cracks identified across the gage section of a specimen that was elongated to 5% strain. Such cracks, which propagated in the direction orthogonal to the applied load, are common when the stress in brittle films exceeds their critical threshold limit. The cracks in FIG. 2A may be distinguished from those at the edges of the specimen, shown in FIG. 2B, which were generated during the sample preparation. Specifically, these edge-located cracks were generated when the alumina ACD coated specimen was cut to size prior to testing. FIG. 2B identifies the unique characteristics of the shear cracks, which quickly arrest near the edge of the specimen. Excellent image contrast was obtained in all of the confocal measurements, allowing cracks to be readily identified despite minimal sample preparation. Field emission scanning electron microscopy (FESEM) was used to measure the width of the cracks. At the fully formed region of the shear cracks, the crack width of about 20 nm was observed using a JSM-7401F field emission scanning electron microscope (JEOL Limited), FIG. 2C.

Example 7

Visualization of Individual Defects and Particles

Figure 3:
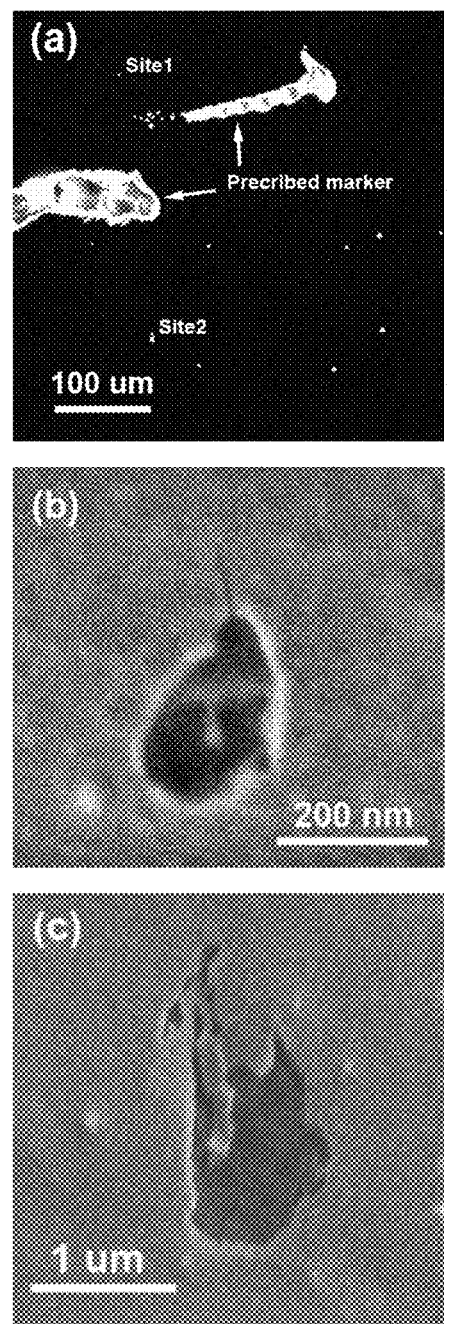
FIG. 3 shows images of individual defects in/on an $Al_2O_3$ ALD film rendered visible by a lipophilic fluorescent tag: (A) defect density and location revealed relative to a marker at low magnification via confocal microscopy; (B, C) details of size and morphology of defects at site #1 and site #2 in (A) identified by high magnification FESEM.

In contrast to mechanical cracks, individual defects or pinholes are generally caused by particulate contamination and/or the substrate surface roughness. Tiny individual defects in submicron/nanoscale size are the critical features limiting barrier performance. These defects have to be inspected and controlled to assure the barrier quality and high yield barrier manufacturing. ALD alumina barrier films were deposited onto PEN substrates and treated with fluorescent tags, as described in Example 5. FIG. 3A is an image collected using a confocal microscope with a 20× objective showing a defect rich region in the 25 nm thick $Al_2O_3$ ALD film. White arrows in FIG. 3A indicate prescribed marker features, used to facilitate defect location for further FESEM imaging. To verify the individual defects and determine the defect size, sites #1 and #2, shown in FIGS. 3B and 3C, respectively, were subsequently observed using FESEM. Diameters of ~200 nm and ~1.2 µm were determined for sites #1 and #2, as indicated in FIGS. 3B and 3C. However, defects smaller than 200 nm also were rendered visible by treatment with the fluorescent tag molecule. The images demonstrate that defect sizes between tens and hundreds of nanometers can be readily visualized after treatment with the lipophilic fluorescent tag substance. FIG. 3 also provides information about the morphology of the individual defects. From FIG. 3B, the oval shaped defect bears a tiny crack at its top end. The defect in FIG. 3C shows a region where the $Al_2O_3$ ALD film was not able to bind to the polymer surface, likely the result of particle contamination. Although the identified defects possibly could be observed using SEM, defect inspection becomes very cumbersome because the defect location as well as the defect density cannot be determined at low magnification. Further, examination at high magnification with small field size is very time-consuming. Compared with SEM and AFM observation, visualization of lipophilic, fluorescent substances according to the present method allows examination of a large field size and offers the advantage of continuous inspection at low magnification.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept and scope of the invention. More specifically, it will be apparent that certain agents which are chemically related may be substituted for the agents described herein while the same or similar results would be achieved. All such similar substitutes and modifications apparent to those skilled in the art are deemed to be within the scope and concept of the invention.

All of the U.S. patents, U.S. patent application publications, U.S. patent applications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

What is claimed is:

1. A material comprising a surface defect, comprising:
 a) a substrate comprising a hydrophobic surface;
 b) a hydrophilic layer covering at least a portion of the hydrophobic surface, wherein the hydrophilic layer comprises a defect that leaves a portion of the hydrophobic surface exposed; and
 c) a lipophilic, fluorescent substance comprising a fluorescent moiety and a lipophilic moiety, wherein the lipophilic, fluorescent substance is in contact with the exposed hydrophobic surface of the substrate.

2. The material of claim 1 wherein the substrate is or comprises a polymer.

3. The material of claim 1 wherein the hydrophilic layer is or comprises an inorganic material.

4. The material of claim 1 wherein the defect has a width or diameter of about 500 nm or less.

5. The material of claim 1 wherein the lipophilic, fluorescent substance comprises two or more lipophilic moieties.

6. The material of claim 1 wherein the lipophilic moiety is a hydrocarbon having 1-20 carbon atoms.

7. The material of claim 1 wherein the lipophilic moiety is an alkyl group having 1-20 carbon atoms.

8. The material of claim 1 wherein the lipophilic moiety is a phenyl or styryl group.

9. The material of claim 1 wherein the lipophilic, fluorescent substance is or comprises a fluorescent dye, fluorescent microparticle or a semiconductor nanocrystal.

10. The material of claim 1 wherein the lipophilic, fluorescent substance comprises a hydrophobic fluorescent dye selected from the group consisting of a p-aminophenyl phosphorylcholine, a naphthalene, an anthracene, a phenanthrene, an indole, a carbazole, a stilbene, a benzimidazole, a benzoxazole, a benzothiazole, a quinoline, a benzoxanthrone, an oxazole, an isoxazole, an oxadiazole, a benzofuran, a pyrene, a perylene, a coronene, a coumarin, a carbostyryl, a bimane, an acridine, a polyphenylene, a phenoxazone, an oxazine, a pyronine, a porphine, a porphyrin, a phthallocyanine and their metallated complexes, a xanthene, a fluorescein, a rhodamine, a cyanine, a carbocyanine, a merocyanine, a rubrene and an azulene, wherein the hydrophobic fluorescent dye is electrically neutral or has ionic charges balanced by lipophilic counter ions.

11. The material of claim 1 wherein the lipophilic, fluorescent substance comprises a hydrophobic fluorescent dye selected from the group consisting of diaza-indacenes, squarenes and styryl dyes.

12. The material of claim 1 wherein the fluorescent moiety is less lipophilic than the lipophilic moiety.

13. A method of identifying a defect in a surface, comprising:
   a) providing a substrate having a hydrophobic surface at least partially coated by a hydrophilic layer, wherein the hydrophilic layer has the defect therein that leaves a portion of the hydrophobic surface exposed;
   b) contacting the substrate with a lipophilic, fluorescent substance comprising a fluorescent moiety and a lipophilic moiety for a sufficient amount of time for the substance to adhere to the exposed hydrophobic surface;
   c) exciting the fluorescent substance with energy at an appropriate wavelength to generate a detectable fluorescence response; and
   d) detecting the fluorescence response of the substance.

14. The method of claim 13, further comprising washing the substrate after contacting the substrate with the lipophilic, fluorescent substance to remove fluorescent substance from the hydrophilic surface.

* * * * *